United States Patent [19]

Henning et al.

[11] Patent Number: 4,684,662
[45] Date of Patent: Aug. 4, 1987

[54] DISUBSTITUTED PROLINE DERIVATIVES

[75] Inventors: Rainer Henning, Frankfurt am Main; Hansjörg Urbach, Kronberg/Taunus, both of Fed. Rep. of Germany

[73] Assignee: Hoechst Aktiengesellschaft, Frankfurt, Fed. Rep. of Germany

[21] Appl. No.: 568,423

[22] Filed: Jan. 5, 1984

[30] Foreign Application Priority Data

Jan. 7, 1983 [DE] Fed. Rep. of Germany ....... 3300316

[51] Int. Cl.$^4$ .................. C07D 209/18; C07D 209/52
[52] U.S. Cl. ..................................... 548/452; 548/530
[58] Field of Search ............................... 548/530, 452

[56] References Cited

U.S. PATENT DOCUMENTS 4,350,704 9/1982 Hoefle et al. ...................... 514/412

FOREIGN PATENT DOCUMENTS 050850 10/1981 European Pat. Off. .
315190 7/1983 Fed. Rep. of Germany .

OTHER PUBLICATIONS

Vincent et al., Tetrahedron Letters, vol. 23, No. 16, pp. 1677–1680 (1982).
Mauger, Witkop, Chemical Reviews, vol. 66, 1966, pp. 47–81.

Primary Examiner—Richard L. Raymond
Assistant Examiner—D. B. Springer
Attorney, Agent, or Firm—Finnegan, Henderson, Farabow, Garrett & Dunner

[57] ABSTRACT

The invention relates to compounds of the formula

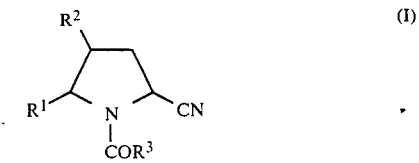

in which $R^1$ and $R^2$ are identical or different and represent alkyl or aryl or together form a C chain and $R^3$ denotes alkyl or aryl, a process for their preparation and their use.

5 Claims, No Drawings

DISUBSTITUTED PROLINE DERIVATIVES

The invention relates to compounds of the formula I

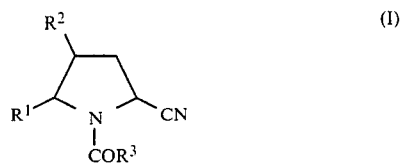

in which

R$^1$ and R$^2$ are identical or different and represent straight-chain or branched alkyl having 1 to 6 carbon atoms or represent (C$_6$ to C$_{10}$)-aryl, preferably phenyl, or together represent one of the chains —(CH$_2$)$_n$— or —(CH$_2$)$_p$—CH=CH—(CH$_2$)$_q$, n, p and q each being an integer, n being 3-6 and (p+q) being 1-4, and R$^3$ denotes straight-chain or branched alkyl having 1 to 5 carbon atoms or (C$_6$ to C$_{10}$)-aryl, preferably phenyl.

It is known that disubstituted proline derivatives can be prepared by various classical methods of aminoacid synthesis. A review of the known work on this topic has been published by A. B. Mauger and B. Witkop (Chem. Rev. 66, 47 (1966)). In the processes described in this reference, the compounds usually result as complex mixtures of isomers. Since certain 4,5-disubstituted isomers which were required as starting compounds for further synthesis could only be obtained in poor yield or not at all by known processes with subsequent separation of isomers, the object was to search for new synthetic routes leading to isomers of this type.

The proline derivatives of the formula I according to the invention are valuable intermediate products in a synthetic route of this type. Preferred compounds of the formula I are those in which R$^1$ and R$^2$ together form one of the abovementioned chains and have the trans configuration with respect to one another. If R$^1$ and R$^2$ are not linked together by a chain, these radicals can have the cis or trans configuration with respect to one another and to the CN group.

The compounds of the formula I can occur in the diastereomeric forms Ia-d, it being possible to represent the relative configurations of these by the following formulae:

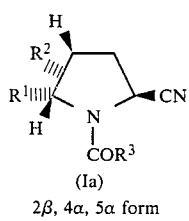 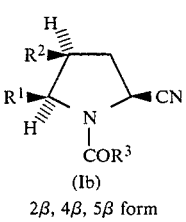

(Ia) 2β, 4α, 5α form    (Ib) 2β, 4β, 5β form

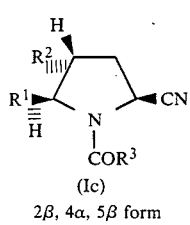 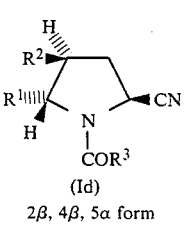

(Ic) 2β, 4α, 5β form    (Id) 2β, 4β, 5α form

The specification "α" means that the substituent in the relevent position is beneath the plane of the five-membered ring and the specification "β" means that it is above this plane. If R$^1$ and R$^2$ are connected together, the numbering is modified to accord with the conventions for bicyclic ring systems.

The invention also relates to a process for the preparation of compounds of the formula I in which R$^1$, R$^2$ and R$^3$ have the abovementioned meanings, which comprises reacting an organomercury compound of the formula II

in which R$^1$, R$^2$ and R$^3$ have the abovementioned meaning and X denotes halogen, preferably chlorine or bromine, pseudohalogen or acetate, with 2-chloroacrylonitrile and sodium borohydride or potassium borohydride to give a compound of the formula III

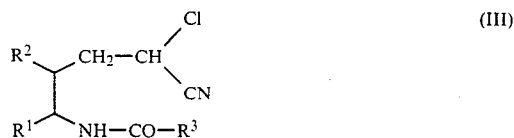

in which R$^1$, R$^2$ and R$^3$ have the abovementioned meaning.

The reaction is carried out in an alcoholic solvent, preferably ethanol, with a one to fifteen-fold, preferably a three to eight-fold, excess of 2-chloroacrylonitrile, at −20° C. to 60° C., preferably at 0° C. to 30° C.

The compound of the formula III is then cyclized to give the compound of the formula I by reaction with a suitable base, preferably sodium hydride in an aprotic dipolar solvent, such as dimethyl sulfoxide or dimethylformamide, or with potassium carbonate or potassium hydroxide in an aprotic solvent, such as, preferably, acetonitrile, with the addition of a phase-transfer catalyst, preferably triethylbenzylammonium chloride, at −20° C. to 80° C., preferably at 0° C. to 40° C.

The invention also relates to compounds of the formula III in which R$^1$, R$^2$ and R$^3$ have the abovementioned meaning.

Moreover, the invention relates to the use of compounds of the formula I, in which R$^1$, R$^2$ and R$^3$ have the abovementioned meaning, in a process for the preparation of compounds of the formula IV

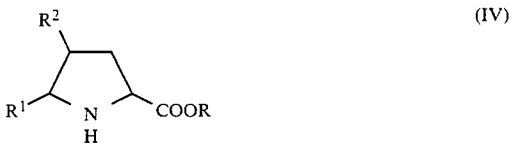

in which R$^1$ and R$^2$ have the abovementioned meanings and R represents hydrogen, alkyl having 1 to 10 carbon atoms, aralkyl having 7 to 9 carbon atoms, cycloalkyl having 5 to 10 carbon atoms, alkylcycloalkyl having 6 to 12 carbon atoms or cycloalkylalkyl having 6 to 12 carbon atoms, which comprises subjecting the compounds of the formula I to solvolysis with compounds of the formula ROH in which R has the above meaning.

Hydrolysis is preferred. For this, the compounds of the formula I are converted in the presence of a strong acid, preferably a mineral acid such as hydrochloric acid or hydrobromic acid, in aqueous solution at 20° C. to 160° C., preferably at 70° C. to 120° C., into the aminoacids of the formula IV in which R denotes hydrogen.

The resulting mixtures of isomers can be separated into the isomers at the various stages in the process (compounds of the formulae III, I and IV) by methods of separation known per se, such as, for example, fractional crystallization or column chromatography.

The starting materials for the preparation of compounds of the formula I are known from J. Prakt. Chem. 311, 737 (1969) and from J. Org. Chem. 41, 192 (1976): they are produced by addition of a mercury salt and a nitrile to the double bond of an olefin of the formula V in which $R^1$ and $R^2$ have the abovementioned meaning.

　(V)

The addition of the two components to the double bond takes place from opposite sides. The result of this is that, starting from cis-disubstituted olefins of the formula Va

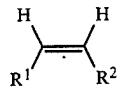　(Va)

the trans-disubstituted compounds of the formula Iva are obtained

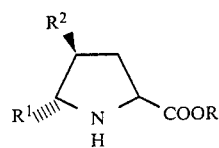　(Iva)

since the steps in the process according to the invention take place with retention of the configuration at each carbon atom. In analogy, starting from trans-disubstituted olefins of the formula Vb

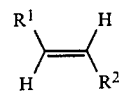　(Vb)

the cis-disubstituted compounds of the formula Ivb are obtained

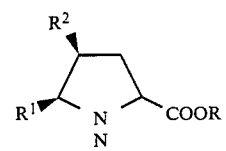　(Ivb)

and starting from cycloolefins of the formulae VIa and VIb respectively

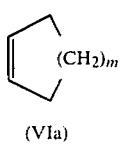　(VIa)　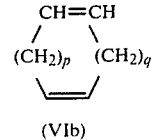　(VIb)

in which m denotes a number from 1 to 4, bicyclic compounds of the formulae VIIa and VIIb respectively are obtained

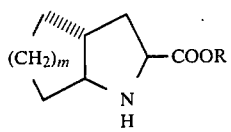　(VIIa)

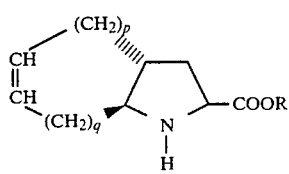　(VIIb)

the two rings in these being linked together trans.

The compounds of the formulae I and IV are valuable intermediate products in the preparation of pharmaceuticals, especially of inhibitors of the angiotensin converting enzyme (ACE). Compounds of this type are known, for example, from European Patent Application No. 50,800, and German Patent Application No. P 3,151,690.4 also relates to them.

Examples of ACE inhibitors of this type are substituted acyl derivatives of the formula VIII

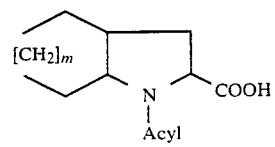　(VIII)

in which m is defined as above and acyl represents, for example, a radical of the formula IX

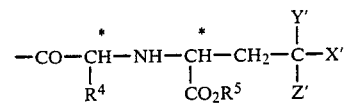　(IX)

in which $R^4$ denotes hydrogen, $(C_1-C_6)$-alkyl which can optionally be substituted by amino, $(C_1-C_4)$-acylamino or benzoylamino, $(C_2-C_6)$-alkenyl, $(C_5-C_9)$-cycloalkyl, $(C_5-C_9)$-cycloalkenyl, $(C_5-C_7)$-cycloalkyl-$(C_1-C_4)$-alkyl, aryl or partially hydrogenated aryl, each of which can be substituted by $(C_1-C_2)$-alkyl, $(C_1-C_2)$-alkoxy or halogen, aryl-$(C_1-C_4)$-alkyl, the aryl radical of which can be substituted as defined above, a monocyclic or bicyclic heterocyclic radical having 5 to 7 or 8 to 10 ring atoms, 1 to 2 of these ring atoms being sulfur or oxygen atoms and/or 1 to 4 of these ring atoms being nitrogen atoms, or a side chain of a naturally occurring aminoacid, $R^5$ denotes hydrogen, $(C_1-C_6)$-alkyl, $(C_2-C_6)$-alkenyl or aryl-$(C_1-C_4)$-alkyl, Y' denotes hydrogen or hydroxyl,
Z' denotes hydrogen or
Y' and Z' together denote oxygen,
X' denotes $(C_1-C_6)$-alkyl, $(C_2-C_6)$-alkenyl, $(C_5-C_9)$-cycloalkyl, aryl which can be monosubstituted, disubstituted or trisubstituted by $(C_1-C_4)$-alkyl, $(C_1-C_4)$-alkoxy, hydroxyl, halogen, nitro, amino, $(C_1-C_4)$-alkylamino, di$(C_1-C_4)$-alkylamino or methylenedioxy, or 3-indolyl, and their physiologically acceptable salts.

Compounds of the formula VIII can be prepared by N-acylation of compounds of the formula IV, in which $R^1$ and $R^2$ have the abovementioned meaning and R has the above meaning with the exception of that of hydrogen, with compounds of the formula acyl-OH, in which acyl is defined as above, and subsequent hydrogenolytic, acid or base elimination of the radicals R and, if appropriate, $R^5$.

The condensation of the compounds of the formula acyl-OH with the esters of the formula IV preferably takes place by processes known from peptide chemistry. Those processes which provide adequate protection from racemization, such as, for example, the DCC/HOBt method or the alkanephosphonic anhydride method described in German Offenlegungsschrift No. 2,901,843, are particularly preferred.

The compounds of the general formula VIII have a long-lasting and potent hypotensive effect. They are well absorbed after oral administration and can be employed to control hypertension of various etiologies and can be used alone or combined with other compounds having hypotensive, vasodilator or diuretic activity. Administration can be intravenous, subcutaneous or oral, oral administration being preferred. The dosage on oral administration is 0.01–10 mg/kg per day, preferably 0.05–1.5 mg/kg per day, especially 0.05–0.5 mg/kg per day.

The dose can also be raised in severe cases, since no toxic properties have hitherto been observed. It is also possible to decrease the dose and this is particularly appropriate when diuretics are administered concurrently. For intraveneous or subcutaneous administration, the single dose should be between 0.1 and 250 μg/kg per day.

The following examples are intended to illustrate the invention.

EXAMPLE 1

2β,3a α,7aβ-Octahydroindole-2-carboxylic acid (a) trans-1-Acetamido-2-chloromercuriocyclohexane 20 ml (0.2 mole) of cyclohexene in 50 ml of acetonitrile are added dropwise over the course of 20 minutes to a suspension of 65 g (0.2 mole) of mercury(II) nitrate in 150 ml of acetonitrile at 0° C. After 1 hour at room temperature, the yellow solution is poured into a mixture of 100 ml of saturated sodium chloride solution and 500 ml of water; the precipitated product is filtered off with suction, washed with water and dried in vacuo. 75 g of colorless crystals of melting point 200°–201° C. are obtained.

(b) trans-1-Acetamido-2-(2-chloro-2-cyanoethyl)cyclohexane 31 g of trans-1-acetamido-2-chloromercuriocyclohexane are suspended in 250 ml of 95% strength ethanol: 187 ml (4 equivalents) of 2-chloroacrylonitrile are added. While cooling in ice, a solution of 3 g of sodium borohydride in 50 ml of ethanol is added as rapidly as possible. After warming up to room temperature, the precipitated elemental mercury is filtered off with suction over kieselguhr, thoroughly washed with ethanol and the filtrate is evaporated. The residue is taken up in methylene chloride, washed three times with 1N sodium hydroxide solution to destroy the boric esters, dried over sodium sulfate and evaporated. 13 g of the title compound are obtained as a yellow oil.

(c) 1-Acetyl-2-cyano-trans-octahydroindole 3.2 g of trans-1-acetamido-2-(2-chloro-2-cyanoethyl)-cyclohexane are dissolved in 25 ml of dimethylformamide and added dropwise, at 0° C., to a suspension of 0.7 g of sodium hydride (50% in oil, washed three times with hexane) in 10 ml of dimethylformamide. After 1 hour at room temperature, the mixture is poured into water, acidified with 5N hydrochloric acid and extracted with methylene chloride. The extract is washed four times with water, dried over sodium sulfate and evaporated. The crude product contains a mixture of 18.5 parts of the 2β, 3aα,7aβ isomer and 1 part of the 2β,3aβ,7aα isomer. On trituration with diisopropyl ether, 0.7 g of the 2β, 3aα, 7aβ isomer crystallizes out. Chromatography of the mother liquor on silica gel using acetic acid/cyclohexane (2:1) as the mobile phase provides a further 0.2 g of the 2β,3aα,7aβ isomer and 45 mg of the 2β,3aβ,7aα isomer.

Physical data: 2β,3aα,7aβ isomer: Melting point 110°–113° C.

$^1$NMR data (270 MHz, DMSO-$d_6$, 100° C.): δ=4.90 (d.J=5 Hz, 1H); 3.05 (dt, J$_1$=5 Hz, J$_2$=1.5 Hz, 1H); 2.60 (d, 1H); 2.17 (d, 1H); 2.03 (s, 3H); 1.95 (broad, d, 1H); 1.85–1.6 (m, 4H); 1.4–1.0 (m, 4H) ppm. MS (m/e): 192 (M+, 32%); 150 (M—CH$_2$=C=O, 59%); 149 (18%); 139 (14%) 107 (100%); 95 (15%); 43 (39%).

2β,3aβ,7aα isomer: oil.

$^1$NMR data (270 MHz, DMSO-$d_6$, 100° C.): δ=4.66 (t, J=5 Hz, 1H); 3.10-3.0 (m, 1H); 2.75-2.6 (m, 1H); 2.08 (s, 3H); 2.0–1.4 (m, 5H); 1.4–1.2 (m, 4H) ppm.

(d) 2β,3aα,7aβ-octahydroindole-2-carboxylic acid 2.8 g of 2β,3aα,7aβ-1-acetyl-2-cyanooctahydroindole are boiled under reflux with 30 ml of 5N hydrochloric acid for 4 hours, evaporated to dryness, the residue is taken up with water, the pH is adjusted to 4.7 with a weakly basic ion exchanger (Amberlite ® IRA 93, OH form), this is filtered off, the filtrate is evaporated, the residue is taken up with ethanol, and acetone is added to precipitate. Filtration with suction and drying provides 1.9 g of the title compound of melting point 286°–288° C. (decomposition).

$^1$NMR data (D$_2$O, 270 MHz): δ=4.15 (d, J=5 Hz, 1H); 2.88 (dd, J$_1$=12 Hz, J$_2$=3.8 Hz, 1H); 2.55 (mc, 1H); 2.3–1.1 (m, 10H) ppm.

EXAMPLE 2

2β,3aα,7aβ-Octahydrocyclopenta[b]pyrrole-2-carboxylic acid (a) trans-1-Acetamido-2-chloromercuriocyclopentane 10 ml of cyclopentene in 30 ml of acetonitrile are added dropwise to a suspension of 38.3 g of mercury(II) nitrate in 80 ml of acetonitrile at 0° C. After 1 hour at room temperature, the mixture is poured into a mixture of 60 ml of saturated sodium chloride solution and 250 ml of water, and the solid is filtered off with suction, washed with water and dried. 26 g of the title compound are obtained as an amorphous powder.

(b) trans-1-Acetamido-2-(2-chloro-2-cyanoethyl)cyclopentane 16.1 g of trans-1-acetamido-2-chloromercuriocyclopentane are suspended in 200 ml of ethanol. 10.7 ml of 2-chloroacrylonitrile are added, followed by 1.7 g of sodium borohydride in 40 ml of ethanol as rapidly as possible while cooling in ice. After 1 hour at room temperature, the mixture is filtered with suction through kieselguhr, the filtrate is evaporated, the residue is taken up with methylene chloride, this solution is washed twice with 1N sodium hydroxide solution, and the organic phase is dried over sodium sulfate and evaporated. Chromatography on silica gel (mobile phase ethyl acetate) produces 2.2 g of crystalline product, melting point 114°–117° C.

$^1$H NMR data (CDCl$_3$): δ=5.4 (broad s, 1H); 4.67 (t, J=7 Hz); 3.95 (mc, 1H); 2.6–1.0 (m, 9H); 1.97 (s, 3H) ppm.

MS (m/e): 214 (M+, 8%); 179 (10%) 140 (20%); 137 (35%); 98 (48%); 60 (78%); 56 (100%); 43 (68%).

(c) 1-Acetyl-2-cyano-trans-octahydrocyclopenta[b]pyrrole 0.75 g of trans-1-acetamido-2-(2-chloro-2-cyanoethyl)cyclopentane is dissolved in 20 ml of DMF and added to 200 mg of sodium hydride (50% in oil, washed twice with hexane) and the mixture is stirred at room temperature for 1 hour. It is then poured into 1N hydrochloric acid, extracted with methylene chloride, and the organic phase is washed four times with water, dried and evaporated. Chromatography on silica gel with ethyl acetate/cyclohexane (2:1) as the mobile phase provides 0.12 g of the 2β,3aβ,6aα isomer as an oil and 0.45 g of the 2β,3aα,6aβ isomer as colorless crystals of melting point 115–°117° C.

$^1$NMR data (CDCl$_3$): δ=5.02 (d, J=7.5 Hz, 1H); 3.33 (dt, J$_1$=11 Hz, J$_2$=6 Hz, 1H); 2.9–1.0 (m, 9H); 2.07 (s, 3H) ppm.

(d) 2β,3aα,6aβ-Octahydrocyclopenta[b]pyrrole-2-carboxylic acid 0.45 g of 2β,3aα,6aβ-1-acetyl-2-cyanooctahydrocyclopenta[b]pyrrole are heated to reflux for 3 hours with 5 ml of 5N hydrochloric acid, then evaporated to dryness, the residue is taken up with water, the pH is adjusted to 6 with a weakly basic ion exchanger (Amberlite ® IRA 93, OH form), this is filtered off, the filtrate is evaporated and crystallized with ethanol/ether.

Yield: 0.26 g
Melting point: >250° C. (decomposition)
$^1$H NMR data (D$_2$O): δ=4.5 (t, 1H); 3.6–3.0 (m, 1H); 2.6–1.0 (m, 9H) ppm. MS (m/e): 155 (M+, 1%); 154 (M+7H, 3%); 110 (M+—COOH, 100%); 67 (24%).

EXAMPLE 3

1-Acetyl-2-cyano-4,5-cis-diethylpyrrolidine (a) erythro-3-Acetamido-4-chloromercuriohexane 39 g of mercury(II) nitrate are suspended in 50 ml of acetonitrile, and 10 g of trans-3-hexene in 20 ml of acetonitrile are added dropwise at 0° C. After 45 minutes at room temperature, the mixture is poured into 500 ml of saturated sodium chloride solution. The title compound initially separates out as an oil, but crystallizes completely after a short time. Melting point Yield 41.5 g.

(b) 2-Chloro-threo-5-acetamido-4-ethylheptanonitrile 15 g of erythro-3-acetamido-4-chloromercuriohexane and 9.6 ml of 2-chloroacrylonitrile are dissolved in 250 ml of ethanol. 1.52 g of sodium borohydride is added rapidly while cooling in ice. After 45 minutes, the elemental mercury formed is filtered off with suction through kieselguhr, the filtrate is evaporated, the residue is taken up with methylene chloride, and the solution is washed three times with 1N sodium hydroxide solution, dried over magnesium sulfate and evaporated. 6.6 g of a 1:1 mixture of the isomers at the 2 position are obtained.

(c) 1-Acetyl-2-cyano-4,5-cis-diethylpyrrolidine 6.6 g of 2-chloro-threo-5-acetamido-4-ethylheptanonitrile are dissolved in 100 ml of dimethylformamide and added dropwise at 0° C. to 1.7 g of sodium hydride (50% in oil, washed 2× with hexane). After 2 hours at room temperature, the mixture is poured into 1N hydrochloric acid and this is extracted twice with methylene chloride. The organic phase is washed four times with water, dried and evaporated. 4.6 g of a brown oil are obtained, from which the two isomers of the title compound are isolated by column chromatography on silica gel using ethyl acetate/cyclohexane (2:1) as the mobile phase.

Isomer 1 (1.63 g)
2β,4β,5β form: R$_f$ value (ethyl acetate/cyclohexane 4:1) 0.5: oil; $^1$H NMR data: 5.0–4.4 (m, 1H); 4.0–3.3 (m, 1H); 2.6–0.7 (m, 13H); 2.15+2.12 (2s, 3H) ppm. MS (m/e): 194 (M+, 8%), 165 (M+—C$_2$H$_5$, 4%); 123 (M+—CH$_3$CO—C$_2$H$_5$, 100%); 43 (17%).

Isomer 2 (1.63 g)
2β,4α,5α form: R$_f$ value (ethyl acetate/cyclohexane 4:1) 0.43, melting point 144°–149° C.: $^1$H NMR data: 5.8–5.4 (m, 1H); 4.3–3.9 (m, 1H); 3.0–2.5 (m, 1H); 2.03 (s, 3H); 2.2–1.1 (m, 6H); 1.08+0.97 (2t, 6H) ppm: MS (m/e): 194 (M+, 8%), 165 (M+—C$_2$H$_5$, 4%), 123 (M+—CH$_3$CO—C$_2$H$_5$, 100%); 43 (14%).

EXAMPLE 4

2β,4β,5β-Diethylproline 1.63 g of 2β,4β,5β-1-acetyl-2-cyano-4,5-diethylpyrrolidine (Example 3c, isomer 1) are heated to reflux for 2.5 hours with 20 ml of 5N hydrochloric acid. After evaporation to dryness, the pH is adjusted to 6 using Amberlite ® IRA 93 (OH⁻ form), and the mixture is filtered, evaporated, the residue is taken up with ethanol/acetone and filtered with suction. Purification is by chromatography on silica gel using methylene chloride/methanol/glacial acetic acid/water (10:3:1:1) as the mobile phase. 1.05 g of the title compound of melting point 230°–235° (decomposition) is obtained.

$^1$NMR data (D$_2$O): δ=4.1 (t, J=9 Hz, 1H); 3.25 (dt, J$_1$=7 Hz, J$_2$=6 Hz, 1H); 2.9–1.0 (m, 7H); 1.0 (t, J=7 Hz, 6H) ppm.

MS (m/e): 171 (M+, 2%); 142 (M+—C$_2$H$_5$, 100%); 126 (M+—COOH, 74%); 115 (12%); 96 (30%); 83 (10%); 69 (33%); 55 (19%).

EXAMPLE 5

2β,4α,5α-Diethylproline 1.63 g of 2β,4α,5α-1-acetyl-2-cyano-4,5-diethylpyrrolidine (Example 3c, isomer 2) are reacted with 20 ml of 5N hydrochloric acid in accordance with the process described in Example 4. 0.72 g of the title compound of melting point 158°–162° C. is obtained.

$^1$H NMR data (D$_2$O): δ=4.15 (t, J=8 Hz, 1H); 3.68 (q, J=6 Hz, 1H); 2.15–1.1 (m, 7H); 1.0 (t, J=7 Hz, 6H) ppm.

MS (m/e): 171 (M$^+$, 1%); 142 (M$^+$—C$_2$H$_5$) 100%); 126 (M$^+$—CO$_2$H, 96%); 115 (19%); 96 (33%); 83 (11%); 69 (36%); 55 (22%).

EXAMPLE 6

1-Acetyl-2-cyano-4,5-cis-dimethylpyrrolidine

Prepared from trans-2-butene in analogy to the procedures described in Example 3a to c.

EXAMPLE 7

4,5-cis-Dimethylproline

Prepared from 1-acetyl-2-cyano-4,5-cis-dimethylpyrrolidine in analogy to the procedure described in Example 4.

EXAMPLE 8

1-Acetyl-2-cyano-4,5-trans-dimethylpyrrolidine

Prepared from cis-2-butene in analogy to the procedures described in Example 3a to c.

EXAMPLE 9

4,5-trans-Dimethylproline

Prepared from 1-acetyl-2-cyano-4,5-trans-dimethylpyrrolidine in analogy to the procedures described in Example 4.

EXAMPLE 10

2β,3aα,8aβ-Decahydrocyclohepta[b]pyrrole-2-carboxylic acid

Prepared from cycloheptene in analogy to the procedures described in Example 1a to d.

EXAMPLE 11

2β,3aα,9aβ-Decahydrocycloocta[b]pyrrole-2-carboxylic acid

Prepared from cyclooctene in analogy to the procedures described in Example 1a to d.

We claim:

1. A compound of the formula I

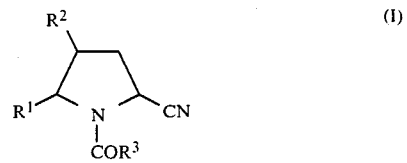

in which
R$^1$ and R$^2$ together represent one of the chains —(CH$_2$)$_n$— or —(CH$_2$)$_p$—CH=CH—(CH$_2$)$_q$, n, p and q each being an integer, n being 3–6 and (p+q) being 1–4, and
R$^3$ denotes a straight-chain or branched alkyl having 1 to 5 carbon atoms or (C$_6$ to C$_{10}$)-aryl wherein the two rings in the compound of formula I are linked together trans.

2. A compound of claim 1 having the formula

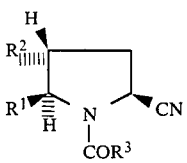

3. A compound of claim 2, wherein R$^3$ is CH$_3$ and n=3 or 4.

4. A compound of claim 3, said compound being 2β,3aα,6aβ-1-acetyl-2-cyano-octahydrocyclopenta[b]pyrrole.

5. A compound of claim 3 said compound being 2β,3aα,7aβ-1-acetyl-2-cyano-octahydroindole.

* * * * *